United States Patent [19]

Carney et al.

[11] 4,198,533

[45] Apr. 15, 1980

[54] (11Z,13Z)-11,13-HEXADECADIEN-1-OL AND DERIVATIVES

[75] Inventors: Robert L. Carney; Clive A. Henrick, both of Palo Alto, Calif.

[73] Assignee: Zoecon Corporation, Palo Alto, Calif.

[21] Appl. No.: 15,277

[22] Filed: Feb. 26, 1979

[51] Int. Cl.$^2$ ............ C07C 33/02; C07C 33/04; C07F 7/18; C07D 309/02
[52] U.S. Cl. .................. 568/840; 260/345.9 R; 568/873; 556/482; 556/471
[58] Field of Search .......... 568/873, 840, 908; 260/345.9 R, 448.8 R

[56] References Cited

U.S. PATENT DOCUMENTS

| 3,072,526 | 1/1963 | Butenandt et al. | 568/840 |
| 3,825,607 | 7/1974 | Descoins et al. | 568/908 |
| 3,856,866 | 12/1974 | Henrick et al. | 568/908 |
| 3,919,329 | 11/1975 | Anderson et al. | 568/908 |
| 3,985,813 | 10/1976 | Labovitz et al. | 568/873 |
| 3,991,125 | 11/1976 | Labovitz et al. | 568/873 |
| 3,996,270 | 12/1976 | Friedman et al. | 260/345.9 |

*Primary Examiner*—Joseph E. Evans
*Attorney, Agent, or Firm*—Donald W. Erickson

[57] ABSTRACT

Synthesis of an attractant (11Z,13Z)-11,13-hexadecadienal for the navel orangeworm *Amyelois transitella*, and intermediates therefor.

3 Claims, No Drawings

(11Z,13Z)-11,13-HEXADECADIEN-1-OL AND DERIVATIVES

This invention relates to the synthesis of an attractant for the navel orangeworm, *Amyelois transitella*, and intermediates.

The compound (11Z,13Z)-11,13-hexadecadienal has been found to be an effective attractant for the navel orangeworm, which is a serious agricultural pest, particularly for almond growers. The foregoing compound has been reported to be the sex pheromone of the female navel orangeworm.

The present invention provides means for the synthesis of (11Z,13Z)-11,13-hexadecadienal and intermediates therefor.

The synthesis of the present invention can be outlined as follows:

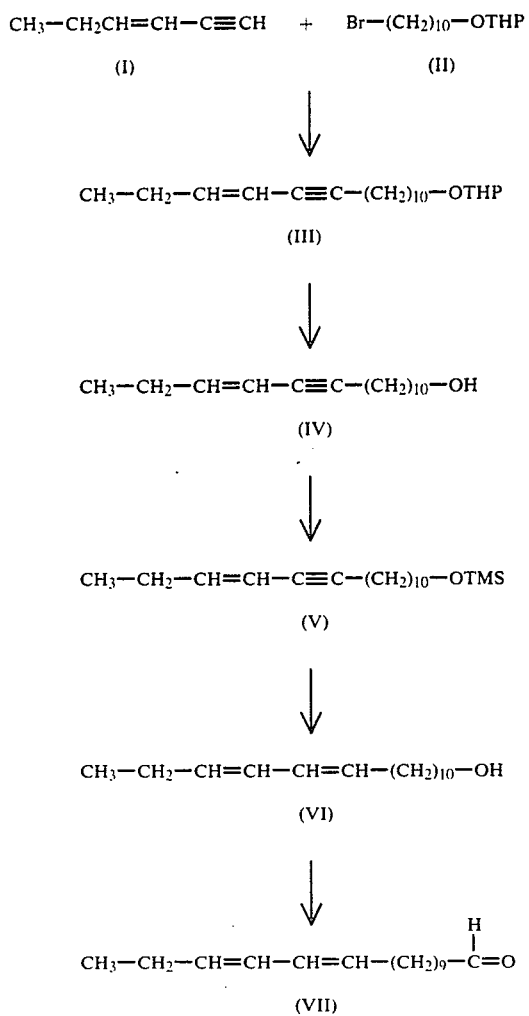

In the practice of the above-outlined synthesis, (3Z)-3-hexen-1-yne (I) is alkylated with the tetrahydropyranyl ether of bromodecanol (II) using lithium amide in liquid ammonia-tetrahydrofuran to yield the tetrahydropyranyl ether of (13Z)-13-hexadecen-11-yl-1-ol (III), which is acid hydrolyzed to the enynol (IV), (13Z)-13-hexadecen-11-yn-1-ol. The enynol (IV) is converted to its trimethylsilyl ether (V) using chlorotrimethylsilane and triethylamine, then is treated with disiamylborane in tetrahydrofuran followed by acetic acid to yield (11Z,13Z)-11,13-hexadecadien-1-ol (VI). The alcohol (VI) is oxidized to the desired aldehyde, (11Z,13Z)-11,13-hexadecadien-1-al (VII) using N-chlorosuccinimide and dimethyl sulfide.

The enyne compound (I) and the bromodecanol tetrahydropyran (II) can be prepared as described by C. A. Henrick, "The Synthesis of Insect Sex Pheromones," Tetrahedron Report No. 34, Pergamon Press Ltd., Oxford, England (1978).

The attractant prepared by the present invention can be used in conjunction with insect traps as part of an integrated pest management program for detection of the navel orangeworm and determination of the need to apply pesticides. The attractant is active at very low levels of the order of 100 to 1,000 micrograms per trap. The attractant can be used by charging a small polyethylene cap or rubber septa which is then placed in a sticky trap.

The following examples are provided to illustrate the practice of the invention. Temperature is given in degrees Centigrade.

EXAMPLE 1

Into about 250 ml of liquid ammonia was added lithium amide (9.2 g, 0.4 mol) in portions followed by (3Z)-3-hexen-1-yne (21.6 g, 0.27 mol) in 20 ml of tetrahydrofuran. After about 15 min, the tetrahydropyranyl ether of 10-bromodecan-1-ol (80.25 g, 0.25 mol) was added. After a few minutes, 100 ml of tetrahydrofurnan was added followed by 7 g of lithium amide. Then, about one-half of the liquid ammonia was evaporated and 100 ml of dry hexamethylphosphoric triamide was added to give a homogenous solution. The mixture was kept under Dry Ice reflux for 7 hours and then 27 g of ammonium chloride was added. Residual ammonia was evaporated, followed by addition of water and hexane. The hexane phase was separated and then evaporated to yield the tetrahydropyranyl ether of (13Z)-13-hexadecen-11-yn-1-ol (III). This material was dissolved in 500 ml of methanol and then 50 ml of 2 N sulfuric acid was added gradually at room temperature. The mixture was degassed and allowed to stand, under nitrogen, at room temperature for about 4 hours. The reaction was concentrated by evaporation and then diluted with water and extracted with hexane. The hexane phase was washed with water and saturated sodium bicarbonate and then solvent evaporated to give crude enynol (IV). The crude enynol was crystallized from hexane at −50°. The enynol was then stirred with a solution of 50 g of urea and 175 ml of hot methanol, which was then cooled, filtered and the solid washed with toluene. The filtrate was concentrated, diluted with water and hexane, and the hexane phase separated and solvent evaporated. The residue was chromatographed on 110 g of Woelm silica using 15% ether in hexane. The material was recrystallized from hexane at −40° to give (13Z)-13-hexadecen-11-yn-1-ol, m.p. 6°-7°.

EXAMPLE 2

To a solution of the enynol IV (32 g, 0.136 mol), 25 ml of triethylamine and 250 ml of hexane was added 21 ml of chlorotrimethylsilane gradually, with stirring and ice bath cooling. After addition was complete, the mixture was stirred at room temperature for about one hour. Then ice water was added and the hexane phase separated and washed with ice-cold 1 N sulfuric acid, saturated sodium bicarbonate and brine. The hexane phase was evaporated to given the trimethylsilyl ether V.

Disiamyl borane was prepared by adding 2-methyl-2-butene (26.7 g, 0.381 mol) to 173 ml of 1 M borane in tetrahydrofurna at ice bath temperature under nitrogen and then allowing the solution to stand at room temperature for about 1.5 hours. This borane solution was transferred gradually through a cannula into a stirred solution of the silyl ether V (0.133 mol) in 50 ml tetrahydrofuran under nitrogen at −15° to −10°. After addition was complete, the solution was held at −5° to 0° for 0.5 hour and then 50 ml of glacial acetic acid was added cautiously, followed by heating at 60° for about 17 hours. Then 50 ml of water and 25 ml methanol were added and the mixture was heated 3 hours. The mixture was cooled in an ice bath as 118 g of 50% aqueous sodium hydroxide was added. To the mixture was added water followed by 30% hydrogen peroxide until the exothermic reaction ceased. The mixture was diluted with hexane and water, washed with aqueous sodium sulfite, separated and the hexane phase evaporated of solvent. The product was recrystallized twice from hexane at −40° to give (11Z,13Z)-11,13-hexadecadien-1-ol, m.p. 31°-32°.

To a mixture of N-chlorosuccinimide (16.8 g, 0.126 mol) and 260 ml of toluene, cooled to 31 20° to −25°, under nitrogen, was added 12.3 ml of dimethylsulfide (10.4 g, 0.167 mol) with stirring. The mixture was stirred for 30 min, then the dienol VI (20 g, 0.0839 mol) in 50 ml of toluene was added gradually over a period of 20 min at −20° to −25°. The mixture was held at −20° for about 20 min, warmed briefly to −5°, then cooled rapidly to −50° and 23.5 ml of triethylamine was added with vigorous stirring. The mixture was warmed to −15° and then to 0°, and after about 10 min 75 ml of water was added. The organic phase was separated, washed with 1 N sulfuric acid, water, dilute sodium bicarbonate and brine, dried over sodium sulfate, and solvent evaporated. The product was chromatographed on 40 g Woelm silica using 10% ether in hexane. The crude aldehyde was crystallized twice from hexane at −50° to yield (11Z,13Z)-11,13-hexadecadien-1-al, m.p. 7°-8°.

What is claimed is:

1. The compound, (13Z)-13-hexadecen-11-yn-1-ol, and the tetrahydropyranyl ether or the trimethylsilyl ether thereof.

2. The compound, (13Z)-13-hexadecen-11-yn-1-ol, according to claim 1.

3. The compound, (11Z,13Z)-11,13-hexadecadien-1-ol.

* * * * *